United States Patent
Isab et al.

(10) Patent No.: US 10,494,394 B1
(45) Date of Patent: Dec. 3, 2019

(54) SYNTHESIS, X-RAY STRUCTURES AND CYTOTOXIC BEHAVIOR OF PLATINUM (II) COMPLEXES OF DITHIOCARBAMATES

(71) Applicant: KING FAHD UNIVERSITY OF PETROLEUM AND MINERALS, Dhahran (SA)

(72) Inventors: Anvarhusein A. Isab, Dhahran (SA); Muhammad Altaf, Dhahran (SA); Muhammad Ali Ehsan, Dhahran (SA); Khalid Omer, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/204,633

(22) Filed: Nov. 29, 2018

(51) Int. Cl.
| | |
|---|---|
| *A61K 31/282* | (2006.01) |
| *C07F 15/00* | (2006.01) |
| *A61K 45/06* | (2006.01) |
| *A61K 9/00* | (2006.01) |
| *A61P 35/00* | (2006.01) |

(52) U.S. Cl.
CPC ........ *C07F 15/0093* (2013.01); *A61K 9/0019* (2013.01); *A61K 31/282* (2013.01); *A61K 45/06* (2013.01); *A61P 35/00* (2018.01)

(58) Field of Classification Search
CPC .......................... A61K 31/282; C07F 15/0093
See application file for complete search history.

(56) References Cited

U.S. PATENT DOCUMENTS

2005/0096304 A1* 5/2005 White ................ A61K 31/27
514/184

FOREIGN PATENT DOCUMENTS

EP 1328267 B1 11/2008

OTHER PUBLICATIONS

Anderson et al. J. Chem. Soc. Dalton Trans., 1982, pp. 2343-2351 (Year: 1982).*
Lin et al. Inorganic Chemistry, 1978, vol. 17, No. 2, pp. 394-401 (Year: 1978).*
Van Der Linden et al. Inorganica Chinnica Acta, 1979, vol. 35, No. 1, pp. 65-71 (Abstract Attached) (Year: 1979).*
Ramos-Espinosa et al. Inorganica Chimica Acta, 2017, vol. 466, pp. 584-590 (Available Online Jul. 15, 2017) (Year: 2017).*
Helm et al. Journal of Ovarian Research, 2009, vol. 2, No. 2, pp. 1-7 (Year: 2009).*
H.S. Sangari, et al. "Platinum Metal Complexes of iV-Ethylcyclohexyldithiocarbamate" Chem. Papers, vol. 51, Issue 5, Oct. 4, 1996, pp. 280-282.
L. Ronconi, et al. "The Midas touch in cancer chemotherapy: from platinum- to gold-dithiocarbamato Complexes" Dalton Transactions, Issue 48, 2009, p. 1 (Abstract Only).
M. Altaf, et al. "New bipyridine gold(III) dithiocarbamate-containing complexes exerted a potent anticancer activity against cisplatin-resistant cancer cells independent of p53 status" Oncotarget, vol. 8, Issue 1, Nov. 18, 2016, pp. 490-505.
C. Donnici, et al. "In Vitro Studies of the Activity of Dithiocarbamate Organoruthenium Complexes against Clinically Relevant Fungal Pathogens" Molecules, vol. 19, Apr. 24, 2014, pp. 5402-5420.
T. Fujie, et al. "Copper diethyldithiocarbamate as an activator of Nrf2 in cultured vascular endothelial cells" J Biol Inorg Chem, vol. 21, Jan. 29, 2016, pp. 263-273.

* cited by examiner

*Primary Examiner* — James D. Anderson
(74) *Attorney, Agent, or Firm* — Oblon, Mcclelland, Maier & Neustadt, L.L.P.

(57) ABSTRACT

The invention is directed to platinum(II) complexes comprising dithiocarbamates and methods for treating cancer using these complexes.

11 Claims, 4 Drawing Sheets

SYNTHESIS, X-RAY STRUCTURES AND CYTOTOXIC BEHAVIOR OF PLATINUM (II) COMPLEXES OF DITHIOCARBAMATES

STATEMENT OF ACKNOWLEDGEMENT

The work described herein was supported by the Deanship of Scientific Research at King Fand University of Petroleum and Minerals under Project No. IN161005.

BACKGROUND

Field of the Invention

The invention pertains to platinum(II) complexes of dithiocarbamates and methods for using them to prevent or treat cancer.

Description of Related Art

The "background" description provided herein is for the purpose of generally presenting the context of the disclosure. Work of the presently named inventor(s), to the extent it is described in this background section, as well as aspects of the description which may not otherwise qualify as prior art at the time of filing, are neither expressly or impliedly admitted as prior art against the present invention.

Cisplatin is a widely used anticancer drug that has been particularly successful in treating testicular, ovarian, small cell lung, head, and neck tumors; V. Brabec, O. Hrabina, J. Kasparkova, Coord. Chem. Rev. 351 (2017) 2-31; T. C. Johnstone, K. Suntharalingam, S. J. Lippard, Chem. Rev. 116 (2016) 3436-3486; S. Dilruba G. V. Kalayda, Cancer Chemother Pharmacol. 77 (2016) 1103-1124; S. Ahmad, Polyhedron 138 (2017) 109-124; G. Y. Ho, N. Woodward, J. I. G. Coward, Crit. Rev. Oncol. Hematol. 102 (2016) 37-46; N. J Wheate, S. Walker, G. E Craig, and R. Oun. Dalton Trans. 39 (2010) 8113-8127; S. Dasari, P. B. Tchounwou, Eur. J. Pharmacol. (2014) 364-378; L. Kelland. Nat Rev Cancer. 7 (2007) 573-584.

The primary target of cisplatin is genomic DNA, specifically the N7 position of guanine bases. This point of attack first generates monofunctional adducts, which subsequently close by binding to the N7 position of an adjacent purine to afford an intrastrand cross-link. These intrastrand cross-links are mainly 1,2-d(GpG) and 1,2-d(ApG), with the 1,2-d(GpG) motif being the dominating feature of the platination reaction; L. Kelland. Nat Rev Cancer. 7 (2007) 573-584; E. R Jamieson, S. J. Lippard, Chem. Rev. 99 (1999) 2467-2498; S. G. Chaney, S. L. Campbell, E. Bassett, Y. Wu, Crit. Rev. Oncol. Hematol. 53 (2005) 3-11; S. Komeda Metallomics 3 (2011) 650-655; Y. Jung, S. J. Lippard, Chem. Rev. 107 (2007) 1387-1407; S. Ahmad, A. Isab, S. Ali, Transition Met. Chem. 31 (2006) 1003-1016. The 1,2-intrastrand cross-links bend and unwind the DNA duplex and after cellular processing suppress DNA transcription efficiently, ultimately leading to cell death; Y. Jung, S. J. Lippard, Chem. Rev. 107 (2007) 1387-1407; S. Ahmad, A. Isab, S. Ali, Transition Met. Chem. 31 (2006) 1003-1016; S. Ahmad, Chem. R. Biodiv. 7 (2010) 543-566; D. Wong, S. J. Lippard, Nature Rev. Drug Disc. 4 (2005) 307-320. However, the use of platinum is restricted because of the severe side effects and due to drug resistance caused by the platinum binding and inactivation of renal thiol containing enzymes; L. Amable, Pharmacol. Res. 106 (2016) 27-36; J. T Hartmann, H. P. Lipp. Expert Opin. Pharmacother. 4 (2003) 889-901; V. M. Piccolini, M. G. Bottone, G. Bottroli, S. A. De Pascali, F. P. Fanizzi, G. Bernocchi, Cell Biol. Toxicol. 29 (2013) 339-353; L. Galluzzi, L. Senovilla, I. Vitale, J. Michels, I. Martins, O. Kepp, M. Castedo, G. Kroemer, Oncogene 31 (2012) 1869-1883; D. J. Stewart, Crit. Rev. Oncol. Hematol. 63 (2007) 12-31.

Dithiocarbamates are among such S-donor ligands that are used as chemoprotectants against nephrotoxicity after cisplatin treatment and diethyldithiocarbamate is usually used to reverse the side effects of cisplatin in cancer chemotherapy; D. Fregona, L. Giovagnini, L. Ronconi, C. Marzano, A. Trevisan, S. Sitran, B. Biondi, F. Bordin, J. Inorg. Biochem. 93 (2003) 181-189; D. L. Bodnner, P. C. Dedon, P. C., Keng and R. F. Borech, Cancer Res. 46 (1986) 2745-2750; Laghari A. J Khuhawar M. Y., Zardari, L. A. & Bhatti, A. G. Chromatographia, 67 (2008) 749-754; K. Lemma, S. K. C. Elmroth and L. I. Elding, J. Chem. Soc., Dalton Trans. (2002) 1281-1286.

Dithiocarbamate complexes of platinum(II) showed remarkable antitumor properties and in some cases their cytotoxic activity was greater than cisplatin; D. Fregona, L. Giovagnini, L. Ronconi, C. Marzano, A. Trevisan, S. Sitran, B. Biondi, F. Bordin, J. Inorg. Biochem. 93 (2003) 181-189; A. G Atanasov, S. Tam, J. M. Rocken, M. E. Baker and A. Odermatt Biochem. Biophys Res. Commun. 308 (2003) 257-262; G. Faraglia, D. Fregona, S. Sitran, L. Giovagnini, C. Marzano, F. Baccichetti, U. Casellato, R. Graziania, J. Inorg. Biochem 83 (2001) 31-40; C. Marzano, A. Trevisan, L. Giovagnini, D. Fregona, Toxicol. in Vitro 16 (2002) 413-419; C. Marzano, D. Fregona, F. Baccichetti, A. Trevisan, L. Giovagnini, F. Bordin, Chem.-Biol. Interact. 140 (2002) 215-229. For example, the compound [Pt(ESDT)(Py)Cl] was proven to be more effective as antiproliferative agent than cisplatin, but with a much lower renal toxicity; G. Faraglia, D. Fregona, S. Sitran, L. Giovagnini, C. Marzano, F. Baccichetti, U. Casellato, R. Graziania, J. Inorg. Biochem. 83 (2001) 31-40. C. Marzano, A. Trevisan, L. Giovagnini, D. Fregona, Toxicol. in Vitro 16 (2002) 413-419. Dithiocarbamates usually coordinate to platinum through two sulfur atoms in a distorted square-planar geometry; C. Marzano, D. Fregona, F. Baccichetti, A. Trevisan, L. Giovagnini, F. Bordin, Chem.-Biol. Interact. 140 (2002) 215-229. M. K. Amir, Zia-ur-Rehman, F. Hayat, S. Z. Khan, G. Hogarth, I. Kondratyuk, J. M. Pezzutode, M. N. Tahir, RSC Advances, 6 (2016) 110517-110524; G. A. Heath, D. C. R. Hockless, P. D. Prenzler, Acta Cryst. C52 (1996) 537-539; D. C. Onwudiwe, J. N. Mugo, M. Hrubaru, E. Hosten, J. Sulfur Chem. 36 (2015) 36-47.

In some cases in addition to chelation to the same metal, the sulfur atom bridges to another metal atom; A. T. Baker, M. T. Emett, Aust. J. Chem. 45 (1992) 429-434. The strong binding of dithiocarbamates to platinum drugs could prevent or at least limit the reaction with other sulfur-containing renal proteins; D. Fregona, L. Giovagnini, L. Ronconi, C. Marzano, A. Trevisan, S. Sitran, B. Biondi, F. Bordin, J. Inorg. Biochem. 93 (2003) 181-189.

The inventors have been involved in synthesizing and studying the anticancer properties of platinum(II) complexes of sulfur donor ligands for the past few years; D. Montagner, P. J. S. Miguel, Dalton Trans. 40 (2011) 10809-10811; A. A. Isab, M. A. J. Ali, S. Sharif, I. U. Khan, S. K. Kang, T. Khalid, M. Saleem, S. Ahmad, Inorg. Chem. Commun. 14 (2011) 1962-1965; A. Z. A. Mustafa, M. Altaf, M. Monim-ul-Mehboob, M. Fettouhi, M. I. M. Wazeer, A. A. Isab, V. Dhuna, G. Bhatia, K. Dhuna, Inorg. Chem. Commun. 44 (2014) 159-163; A. Z. A. Mustafa, M. Monim-ul-Mehboob, M. Y. Jomaa, M. Altaf, M. Fettouhi, A. A. Isab, M. I. M. Wazeer, H. Stoeckli-Evans, G. Bhatia, V. Dhuna, J. Coord.

Chem. 68 (2015) 3511-3524; M. Y. Jomaa, M. Altaf, S. Ahmad, G. Bhatia, J. Singh, S. Altuwaijri, A. A. Isab, Biometals 30 (2017) 787-795; M. Y. Jomaa, M. Altaf, S. Ahmad, A. Alhoshani, N. Baig, A.-N. Kawde, G. Bhatia, J. Singh, A. A. Isab, Polyhedron 141 (2018) 360-368; Seerat-ur-Rehman, A. A. Isab, M. N. Tahir, T. Khalid, M. Saleem, H. Sadaf, S. Ahmad, Inorg Chem Commun. 36 (2013) 68-71. The inventors previously reported the crystal structure of a mixed ligand-platinum(II) complex of pyrrolidinedithiocarbamate (PDTC) and DMSO, [Pt(PDTC)(DMSO)Cl]; D. Montagner, P. J. S. Miguel, Dalton Trans. 40 (2011) 10809-10811.

The inventors have now synthesized three new platinum (II) complexes of dithiocarbamates and investigated their antitumor activity. The complexes were characterized by elemental analysis, IR, $^1$H and $^{13}$C NMR spectra, and two of them, complexes (1) and (2), by single crystal X-ray diffraction technique. The structures of ligands 1, 2, and 3 used to make the complexes are shown below.

BRIEF SUMMARY OF THE INVENTION

A method for treating a proliferative disease, disorder or condition, such as ovarian cancer, in a subject comprising administering to a subject in need thereof at least one complex comprising a platinum atom coordinated with or bound to two dithiocarbamate molecules; especially a complex (1): [Pt(S$_2$CN$^i$Bu$_2$)$_2$], a complex (2): [Pt(S$_2$CNBn$_2$)$_2$] •py, where py=Pyridine); or a complex (3): [Pt(S$_2$CN$^i$Pr$_2$)$_2$].

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 5A: A2780 S (cisplatin sensitive); FIG. 5B: A2780 CR (cisplatin resistant).

DETAILED DESCRIPTION OF THE INVENTION

The present disclosure will be better understood with reference to the following definitions:

Platinum(II) or Pt(II) describes platinum in an oxidation state of +2. One example of a platinum(II) compound is platinum chloride having the chemical formula PtCl$_2$.

The term dithiocarbamate describes a functional group in organic chemistry which is an analog of a carbamate in which both oxygen atoms are replaced by sulfur atoms. The term "dithiocarbamate moiety" refers to a portion of a complex, such as a platinum-dithiocarbamate complex, derived from the dithiocarbamate.

The term alkyl, as used herein, unless otherwise specified, refers to a straight or branched hydrocarbon fragment, such as a $C_1$-$C_6$ group. Non-limiting examples of such hydrocarbon fragments include methyl, ethyl, propyl, isopropyl, butyl, isobutyl, t-butyl, pentyl, isopentyl, neopentyl, hexyl, isohexyl, 3-methylpentyl, 2,2-dimethylbutyl, and 2,3-dimethylbutyl. In preferred embodiments, when the dithiocarbamate ligands contain alkyl groups, the alkyl groups are branched, more preferably are branched $C_3$-$C_4$ alkyl groups.

As used herein, the term "cycloalkyl" refers to a cyclized alkyl group. Exemplary cycloalkyl groups include, but are not limited to, cyclopropyl, cyclobutyl, cyclopentyl, cyclohexyl, norbornyl, and adamantyl. Branched cycloalkyl groups, for example, methylcyclopropyl and 2-methycyclopropyl groups, are included in the definition of cycloalkyl as used in the present disclosure.

The term "arylalkyl" as used in this disclosure refers to a straight or branched chain alkyl moiety having 1 to 8 carbon atoms that is substituted by an aryl group or a substituted aryl group having 6 to 12 carbon atoms, and includes benzyl, 2-phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, Compositions.

A platinum(II) dithiocarbamate complex of the invention, a salt thereof, a solvate thereof, a prodrug thereof, or a combination thereof may be formulated as a pharmaceutically acceptable composition, for example, with a physiologically acceptable carrier for intravenous administration. As used herein, a "composition" refers to a mixture of the active ingredient with at least one other chemical component, such as a pharmaceutically acceptable carrier or excipient. One purpose of a composition is to facilitate administration of the platinum(II) complex of the invention, the salt thereof, the solvate thereof, the prodrug thereof, or a combination thereof to a subject.

Depending on the intended mode of administration (oral, parenteral, or topical), the composition can be in the form of solid, semi-solid, liquid, or aerosol dosage foil is, such as tablets, suppositories, pills, capsules, powders, liquids, or suspensions, preferably in unit dosage form suitable for single administration of a precise dosage.

The phrase "pharmaceutically acceptable" as used herein refers to compounds, counterions, materials, compositions, and/or dosage forms which are, within the scope of sound medical judgment, suitable for use in contact with the tissues of human beings and animals without excessive toxicity, irritation, allergic response, or other problem or complication and commensurate with a reasonable benefit/risk ratio. A composition is typically a combination of an active ingredient with a carrier or excipient, inert or active, making the composition especially suitable for diagnostic or therapeutic use in vivo, ex vivo, or in vitro.

The term active ingredient, as used herein, refers to an ingredient in the composition that is biologically active, for example, the platinum(II) complexes disclosed herein, a salt thereof, a prodrug thereof, or a solvate thereof. Other active ingredients include, but are not limited to, those that exert a substantial pharmacokinetic or pharmacodynamic activity when in admixture with a platinum(II) complex, for example, other anti-cancer drugs, immunopotentiators, or other agents.

As used herein, a pharmaceutically acceptable carrier refers to a carrier or diluent that does not cause significant irritation to an organism, does not abrogate the biological activity and properties of the administered active ingredient, and/or does not interact in a deleterious manner with the other components of the composition in which it is contained.

The term "carrier" encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9%, a 1:1 mixture of sodium chloride 0.9%/glucose 5%, sodium chloride 0.9% and 1.875% mannitol, for injection, sodium chloride 0.45%, or glucose 2.5% and 1.875% mannitol for injection. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety. Examples of physiologically acceptable carriers include buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS® (BASF; Florham Park, N.J.).

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and nonionic detergents, polyethylene glycols can be used. Mixtures of solvents and wetting ingredients such as those discussed above are also useful.

Other active ingredients. In some embodiments, other active ingredients in addition to the platinum(II) complex may be incorporated into a composition or separately administered in conjunction with a platinum(II) complex. In one embodiment, the composition is used for treating cancer and further comprises a second active ingredient, such as a chemotherapeutic or immunotherapeutic agent, for the treatment or prevention of neoplasm, of tumor or cancer cell division, growth, proliferation and/or metastasis in the subject; induction of death or apoptosis of tumor and/or cancer cells; and/or any other form of proliferative disorder. Exemplary chemotherapeutic agents include, without limitation, aflibercept, asparaginase, bleomycin, busulfan, carmustine, chlorambucil, cladribine, cyclophosphamide, cytarabine, dacarbazine, daunorubicin, doxorubicin, etoposide, fludarabine, gemcitabine, hydroxyurea, idarubicin, ifosfamide, irinotecan, lomustine, mechlorethamine, melphalan, mercaptopurine, methotrexate, mitomycin, mitoxantrone, pentostatin, procarbazine, topotecan, vinblastine, vincristine, retinoic acid, oxaliplatin, carboplatin, 5-fluorouracil, teniposide, amasacrine, docetaxel, paclitaxel, vinorelbine, bortezomib, clofarabine, capecitabine, actinomycin D, epirubicin, vindesine, methotrexate, 6-thioguanine, tipifarnib, imatinib, erlotinib, sorafenib, sunitinib, dasatinib, nilotinib, lapatinib, gefitinib, temsirolimus, everolimus, rapamycin, bosutinib, pzopanib, axitinib, neratinib, vatalanib, pazopanib, midostaurin, enzastaurin, trastuzumab, cetuximab, panitumumab, rituximab, bevacizumab, mapatumumab, conatumumab, and lexatumumab.

The terms "patient", "subject", and "individual" are used interchangeably. As used herein, they refer to individuals suffering from a disease, at risk of further progression of a disease, or at risk of acquiring or developing the disease. None of these terms require that the individual be under the care and/or supervision of a medical professional.

These terms generally refer to humans, but also apply to mammals, avians and other animals, especially domesticated or ecologically or commercially valuable animals. Mammals include non-human primates, such as chimpanzees, and other apes and monkey species, farm animals, such as cattle, horses, sheep, goats, swine, domestic animals, such as rabbits, dogs, and cats, laboratory animals including rodents, such as rats, mice and guinea pigs, and the like. In a preferred embodiment, the subject is a human.

A subject in need of treatment includes a subject already having cancer or a proliferative disease or disorder, a subject who does not yet experience or exhibit symptoms of the disease or disorder, and a subject who is predisposed to the disease or disorder, for example based on family history or genetic profile. In preferred embodiments, the subject is a person who has or is predisposed to cancer such as a person with a family history of cancer. In another embodiment, the subject refers to a cancer patient who has been previously administered/treated with cisplatin or another platinum-based antineoplastic drug and exhibits drug resistance, for example in the form of high ERCC1 mRNA levels, overexpression of HER-2/neu, activation of the PI3-K/Akt pathway, loss of p53 function, and/or overexpression of anti-apoptotic bcl-2).

Antitumor properties may be evaluated by methods known in the art, including these described by and incorporated by reference to Y. F. To, R. W.-Y. Sun, Y. Chen, V. S.-F. Chan, W.-Y. Yu, P. K.-H. Tam, C.-M. Che and C.-L. S. Lin, Int. J. Cancer, 2009, 124, 1971-1979; C. T. Lum, Z. F. Yang, H. Y. Li, R. W.-Y. Sun, S. T. Fan, R. T. P. Poon, M. C. M. Lin, C.-M. Che and H. F. Kung, Int. J. Cancer, 2006, 118, 1527-1538; C. T. Lum, A. S.-T. Wong, M. C. M. Lin, C.-M. Che and R. W.-Y. Sun, Chem. Commun., 2013, 49, 4364-4366; C.-M. Che, R. W.-Y. Sun, W.-Y. Yu, C.-B. Ko, N. Zhu and H. Sun, Chem. Commun., 2003, 1718-1719; Y. Wang, Q.-Y. He, R. W.-Y. Sun, C.-M. Che and J.-F. Chiu, Eur. J. Pharmacol., 2007, 554, 113-122—each incorporated by reference.

Cytotoxic Activity.

In one embodiment, the $IC_{50}$ of the platinum(II) complexes is in a range of 0.01-200 μM, 0.1-100 μM, 1-100 μM, 10-90 μM, 20-80 μM, 30-80 μM, 40-80 μM, 50- or 50-75 μM. These ranges include all intermediate subranges and values.

As used herein, the term "$IC_{50}$" refers to a concentration of a platinum(II) complex, the salt thereof, the prodrug thereof, or the solvate thereof, which causes the death of 50% of cancer or proliferating cells in 72 hours (3 days) such as MCF-7, A2780, A2780R, or 2Rv1 cancer cell lines. The $IC_{50}$ can be determined by standard cell viability assays, such as, without limitation, ATP test, calcein AM assay, clonogenic assay, ethidium homodimer assay, Evans blue assay, Fluorescein diacetate hydrolysis/propidium iodide staining assay, flow cytometry assay, formazan-based assays (MIT, XTT), green fluorescent protein assay, lactate dehydrogenase assay, methyl violet assay, propidium iodide assay, Resazurin assay, Trypan Blue assay and TUNEL assay. Preferably, a MIT assay and/or a Trypan Blue assay are used.

Biomarkers.

Alternatively to use of $IC_{50}$ values, efficacy of treatment with a platinum(II) complex of the invention may be determined by measuring or detecting a change in one or cancer biomarkers, for example, comparing quantity of biomarkers in a blood or tissue sample before and after a treatment.

A treatment may significantly decrease the concentration of a particular biomarker, for example, by 5, 10, 15, 20, 25, 30, 35, 40, 45, 50, 55, 60, 65, 70, 75, 80, 85, 90, or 100%, compared to a control or pre-treatment value. As used herein, the term "biomarker" refers to a characteristic that is objectively measured and evaluated as an indicator of normal biological processes, pathogenic processes or pharmacological responses to a therapeutic intervention. Biomarkers include ER/PR, HER-2/neu for breast cancer, EGFR, KRAS, UGT1A1 for colorectal cancer, EML4/ALK, EGFR, and KRAS for lung cancer as well as other biomarkers described and incorporated by reference to https://_en.wikipedia.org/wiki/Cancer_biomarkers (last accessed Sep. 6, 2018). Cancer biomarkers are useful in determining the aggressiveness of an identified cancer as well as its likelihood of responding to the treatment. Examples of such prognostic biomarkers include, without limitation, CA125, β2-microglobulin, and EBV DNA. A change or mutation in a biomarker may be detected with a polymerase chain reaction (PCR) assay, DNA microarray, multiplex ligation-dependent probe amplification (MLPA), single strand conformational polymorphism (SSCP), denaturing gradient gel electrophoresis (DGGE), heteroduplex analysis, and restriction fragment length polymorphism (RFLP). The procedures to detect the mutation are well-known to those of ordinary skill in the art. The concentration of the biomarker may be measured with an assay, for example an antibody-based method (e.g., an ELISA).

As used herein, the term antibody-based method refers to any method with the use of an antibody including, but not limited to, enzyme-linked immunosorbent assay (ELISA), Western blotting, immunoprecipitation (IP), enzyme linked immunospot (ELISPOT), immunostaining, immunohistochemistry, immunocytochemistry, affinity chromatography, and the like. Preferably, an ELISA is used. The term ELISA refers to a method of detecting the presence and concentration of a biomarker in a sample, for example, before, during or after treatment with a Pt(II) complex of the invention. There are several variants of ELISA, including, but not limited to, sandwich ELISA, competitive ELISA, indirect ELISA, ELISA reverse, and the like. The ELISA assay may be a singleplex assay or a multiplex assay, which refers to a type of assay that simultaneously measures multiple analytes in a single run/cycle of the assay. A sandwich ELISA may be used. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

The term sample includes any biological sample taken from the subject including a cell, tissue sample, or body fluid. For example, a sample may include a tumor sample, skin sample, a cheek cell sample, saliva, or blood cells. A sample can include, without limitation, a single cell, multiple cells, fragments of cells, an aliquot of a body fluid, whole blood, platelets, serum, plasma, red blood cells, white blood cells, endothelial cells, tissue biopsies, synovial fluid, and lymphatic fluid. In some embodiments, the sample is taken from a tumor. In some embodiments, the concentration of the biomarker is measured before and after the administration. When the concentration of the biomarker is maintained, the method may further comprise increasing the effective amount of at least one of the platinum(II) complex of the invention, the salt thereof, the solvate thereof, the prodrug thereof, and the combination thereof by at least 5%, at least 10%, or at least 30%, up to 50%, up to 60%, or up to 80% of an initial effective amount that is in a range of 1-100 mg/kg based on the weight of the subject. The subject may be administered with the increased dosage for a longer period (e.g. 1 week more, 2 weeks more, or 2 months more) than the duration with the initial effective amount. In some embodiments, the mutation in the biomarker is detected before administrating the composition to identify subjects predisposed to the disease. For example, women with a BRCA1 germline mutation are at a higher risk of contracting ovarian cancer. In some embodiments, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

Cancers/Proliferative Disorders. The platinum(II) complexes of the invention may be used to treat cancer or other proliferative disorders. Cancers include but are not limited to, sarcomas, carcinomas, melanomas, myelomas, gliomas and lymphoma (including Hodkin lymphoma). In some embodiments, the Pt(II) complexes of the invention retain anti-cancer activity against cancer cells that are or have become resistant to conventional anti-cancer drugs such as cisplatin. When resistance in a subject or in subject's cancer cells develops to a conventional anticancer drug, treatment may be continued with a Pt(II) complex of the invention to which the cancer cells are sensitive.

In some embodiments, methods incorporating the use a platinum(II) complex of the present disclosure to treat or prevent cancer of the blood, brain, bladder, lung, cervix, ovary, colon, rectum, pancreas, skin, prostate gland, stomach, breast, liver, spleen, kidney, head, neck, testicle, bone, bone marrow, thyroid gland or central nervous system.

In some embodiments, these methods are effective in the treatment or prevention of cervical, colon, prostate, and lung cancers. Cancers or tumor resistant to other anticancer drugs, such as cisplatin-resistant cancers, may be treated. In treating certain cancers, the best approach is often a combination of surgery, radiotherapy, and/or chemotherapy. Therefore, in at least one embodiment, the composition is employed in conjunction with conventional radiotherapy and/or chemotherapy. In another embodiment, the composition is employed with surgery. The radiotherapy and/or surgery may be before or after the composition is administered.

Ovarian carcinoma is a cancer that forms in or on an ovary. It results in abnormal cells that have the ability to invade or spread to other parts of the body. When this process begins, there may be no or only vague symptoms, however symptoms become more noticeable as the cancer progresses. These symptoms may include bloating, pelvic pain, abdominal swelling, and loss of appetite, among others. Common areas to which the cancer may spread include the lining of the abdomen, lymph nodes, lungs, and liver. About 10% of cases are related to inherited genetic risk; women with mutations in the genes BRCA1 or BRCA2 have about a 50% chance of developing the disease. The most common type of ovarian cancer, comprising more than 95% of cases, is ovarian carcinoma. There are five main subtypes of ovarian carcinoma, of which high-grade serous carcinoma is the most common. A diagnosis of ovarian cancer is usually confirmed through a biopsy of tissue, usually removed during surgery. If caught and treated in an early stage, ovarian cancer is often curable. Treatment usually includes some combination of surgery, radiation therapy, and chemotherapy. The Pt(II) complex of the invention may be administered by itself or in combination with other therapy to a subject at risk of ovarian cancer, a subject diagnosed with ovarian cancer, or a subject under treatment for ovarian cancer, or a subject who has already been treated for ovarian cancer, for example, by removal of the ovaries.

Other non-cancerous proliferative diseases, disorders or conditions such as atherosclerosis, rheumatoid arthritis, psoriasis, idiopathic pulmonary fibrosis, scleroderma, cirrhosis of the liver, or benign proliferative conditions such as verruca (warts), dermatitis, or other disorders characterized by epidermal cell proliferation may also be treated.

Therapy.

As used herein, the terms "therapies" and "therapy" can refer to any method, composition, and/or active ingredient that can be used in the treatment and/or management of the disease or one or more symptoms thereof. In some embodiments, the method for treating the disease involves the administration of a unit dosage or a therapeutically effective amount of the active ingredient to a subject in need thereof.

Administration.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection including intravenous, subcutaneous, intraperitoneal, intramuscular, intravascular, or infusion, topical and rectal administration. Typically a composition containing a Pt(II) complex of the invention is administered intravenously or intraperitoneally. Those of ordinary skill in the art are familiar with administration techniques that can be employed with the compounds and methods described herein. In preferred embodiments, the active ingredient and/or the composition described herein are administered orally.

The ter is "effective amount", "therapeutically effective amount", or "pharmaceutically effective amount" refer to that amount of the active ingredient being administered which will relieve to some extent one or more of the symptoms of the disease being treated. The result can be reduction and/or alleviation of the signs, symptoms, or causes of a disease, or any other desired alteration of a biological system. For example, an "effective amount" for therapeutic uses is the amount of the platinum(II) complex of the invention, the salt thereof, the solvate thereof, the prodrug thereof, or a combination thereof as disclosed herein required to provide a clinically significant decrease in a disease. An appropriate "effective amount" may differ from one individual to another. An appropriate "effective amount" in any individual case may be determined using techniques, such as a dose escalation study.

The dosage and treatment duration are dependent on factors, such as bioavailability of a drug, administration mode, toxicity of a drug, gender, age, lifestyle, body weight, the use of other drugs and dietary supplements, the disease stage, or tolerance and resistance of the body to the administered drug, and then determined and adjusted accordingly. In at least one embodiment, the at least one of the platinum (II) complex of the invention, the salt thereof, the solvate thereof, the prodrug thereof, and the combination thereof is administered in an effective amount in a range of 1-100 mg/kg based on the weight of the subject, preferably 10-80 mg/kg, more preferably 20-50 mg/kg. The composition may comprise 0.01-50 µM, 0.01-30 µM, preferably 0.01-10 µM of the platinum(II) complex of the invention relative to the total composition.

Preferably, the method according to the invention will require the administration of a lower amount of the Pt(II)

dithiocarbamate complex of the invention than a corresponding amount of a platinum-based anticancer drug like cisplatin, for example, the dosage of the complex of the invention may be 10, 20, 30, 40, 50, 60, 70, 80, or 90 wt % of the dosage of cisplatin given for a particular type of cancer. Representative cisplatin dosages for treatment of ovarian cancer are 75-100 mg/m² intravenously once every 4 weeks.

In some embodiments, the composition comprises up to 0.1 wt %, 1 wt %, 5 wt %, or 10 wt % of the pharmaceutically acceptable salt of the platinum(II) complex of the invention. In some embodiments, the composition comprises up to 0.1 wt %, 1 wt %, 5 wt %, or 10 wt % of the pharmaceutically acceptable solvate thereof of either the platinum(II) complex of the invention. These ranges include all intermediate subranges and values.

A treatment method may comprise administering a composition containing the platinum(II) complex of the invention as a single dose or multiple individual divided doses. In some embodiments, the composition is administered at various dosages (e.g., a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, 5 days, 6 days, or 7 days. In certain embodiments, the composition and one or more additional therapies are administered less than 1 day, 1 week, 2 weeks, 3 weeks, 4 weeks, one month, 2 months, 3 months, 6 months, 1 year, 2 years, or 5 years apart.

Embodiments of the invention include but are not limited to the following.

A method for treating a proliferative disease, disorder or condition in a subject that includes administering to a subject in need thereof at least one complex comprising a platinum atom coordinated with or bound to two dithiocarbamate molecules. Platinum in the complex is typically in oxidation state (II). The complex itself is free of, or does not include, other metal atoms such as Au, Ag, Cu, Fe or Zn. In typical embodiments, the platinum atom is in oxidation state II or Pt(II) and the dithiocarbamate molecule used to make the complex has the following formula:

where R is, independently, alkyl, aryl, arylalkyl, or other suitable substituents. Advantageously R may be selected to be alkyl or arylalkyl.

A Pt(II) dithiocarbamate complex may conform to the following structure:

where R is hydrogen, alkyl, alkenyl, aryl, or arylalkyl. In some embodiments, alkyl or alkenyl is $C_1$, $C_2$, $C_3$, $C_4$, $C_5$, $C_6$, $C_7$, or $C_8$.

In some embodiments the dithiocarbamate used to produce includes one of the following dithiocarbamates which are used in combination with a Pt atom to produce complexes (1), (2) and (3), respectively:

Na(S₂CNⁱBu₂)

Na(S₂CNⁱBn₂)

Na(S₂CNⁱPr₂)

wherein the R groups are, independently, alkyl or arylalkyl. In some embodiments, the cation Na⁺ may be substituted with another cation such as K. In some embodiments the cation is monovalent or divalent. Preferably both R groups in a Pt-dithiocarbamate complex are the same. Some representative Pt-dithiocarbamate complexes include complex (1): [Pt(S₂CNⁱBu₂)₂], complex (2): [Pt(S₂CNBn₂)₂]·py, where py=pyridine) and complex (3): [Pt(S₂CNⁱPr₂)₂].

In a method according to the invention a Pt-dithiocarbamate complex, such as complex (1), (2) or (3), may be administered to a subject having, or at risk of developing a cancer or another proliferative disease, disorder or condition. A cancer or other proliferative disease, disorder or condition may be one that is resistant to or unresponsive to cisplatin or another platinum-based antineoplastic or antiproliferative drug or agent. In some embodiments, the proliferative disease, disorder or condition is sarcoma, carcinoma (e.g., small cell lung cancer, cervical cancer, and a gem cell tumor. In some embodiments, the proliferative disease, disorder, or condition is ovarian cancer.

In other embodiments, the cancer may be prostate cancer, breast cancer, The method of embodiment 1, wherein the proliferative disease, disorder, or condition is prostate cancer, testicular cancer, cervical cancer, bladder cancer, head and neck cancer, esophageal cancer, lung cancer, mesothelioma, a brain tumor or neuroblastoma.

A Pt-dithiocarbamate complex of the invention may be administered to a subject in need thereof by any suitable mode of administration that subjects the target cells to direct or indirect action of the complex. Typically, the complex is administered intravenously, intraperitoneally, or by other parenteral route. In one embodiment a dosage of about 50-150 mg/m$^2$ in 0.9% sodium chloride, lactated Ringer's solution or other physiological acceptable solution may be administered every 2, 3, 4, 5, 6, 7, or 8 weeks.

In some embodiments a subject in need of treatment exhibits bone marrow suppression, neurotoxicity, ototoxicity or hearing problems, nephrotoxicity or kidney problems, electrolyte disturbance, nausea, vomiting, numbness, trouble walking, allergic reactions, electrolyte problems (e.g., hypomagnesaemia, hypokalaemia and hypocalcaemia), and/or heart disease when treated with cisplatin or another platinum-based antineoplastic drug. In other embodiments a subject will be resistant to cisplatin or another platinum-based anticancer drug, for example, as characterized by changes in cellular uptake and efflux of the anticancer drug, increased detoxification of the drug, inhibition of apoptosis or increased DNA repair.

Another embodiment of the invention is directed to a [Pt(dithiocarbamate)$_2$] complex comprising a platinum atom and two dithiocarbamates, wherein the two dithiocarbamates have the following structure:

wherein R is hydrogen, alkyl, alkenyl, aryl, arylalkyl or another suitable group that produces a complex exhibiting anticancer or antiproliferative activity. Preferably, each R is the same. Some representative R groups include isobutyl, benzyl and isopropyl. Such a complex may have the following chemical structure, where the R groups derived from the thiocarbamates are defined above:

Another embodiment of the invention is directed to a pharmaceutical composition that includes, consists essentially of, or consists of at least one platinum(II)-dithiocarbamate complex as described herein in combination with at least one pharmaceutically acceptable carrier or excipient. In some embodiments, a pharmaceutical composition further includes at least one other anticancer drug, chemotherapeutic agent, or immunopotentiator.

Examples

The following examples illustrate various aspects of the present invention. They are not to be construed to limit the claims in any manner whatsoever.

Platinum(II) complexes of dithiocarbamates (L) with the general formula, [Pt(L)$_2$] have been prepared and characterized using elemental analysis, IR, and $^1$H NMR spectroscopy {L=diisobutyldithiocarbamate (S$_2$CN$^i$Bu), dibenzyldithiocathamate (S$_2$CNBn$_2$), and diisopropyldithiocarbamate (S$_2$CN$^i$Pr$_2$). The crystal structures of [Pt(S$_2$CN$^i$Bu$_2$)$_2$] (1) and [Pt(S$_2$CNBn$_2$)$_2$].py (2) (py=pyridine) were determined by single X-ray diffraction analysis. The structures of (1) and (2) consist of neutral molecules. The platinum atom in both the complexes adopts a distorted square planar geometry. The spectroscopic data indicated the coordination of dithiocarbamate ligands to platinum(II). The in vitro cytotoxicity of three of these compounds as well as of cisplatin was tested using MTT assay against two human ovarian tumor cell lines, which are; A2780 S (cisplatin sensitive); A2780 CR (cisplatin resistance). The in vitro cytotoxicity of all three platinum(II) complexes was found to be lower than cisplatin.

Materials.

Platinum chloride (PtCl$_2$) and dithiocarbamates as sodium salts were purchased from Sigma Aldrich and were used as received. (3-(4,5-Dimethylthiazol-2-yl)-2,5-diphenyltetrazolium bromide, a yellow tetrazole) was obtained from Sigma Chemical Co, St. Louis, Mo., USA.

General Procedure for the Synthesis of [Pt(Dithiocarbamate)$_2$] Complexes (1-3).

For the preparation of complexes, two equivalents of sodium salts of dithiocarbamates (2 mmol) and platinum(II) chloride (0.26 g, 1 mmol) were dissolved in methanol (50 mL) and the resultant dark yellow solution was stirred for 30 minutes. The solutions were filtered and kept at room temperature for crystallization. Yellow or brown crystals were obtained on slow evaporation of the solvent. In the case of dibenzyl derivative (complex 2) 30 mL pyridine (py) was added to give a clear yellow solution and stirring was continued for another hour. Filtration and slow evaporation of the reaction mixture afforded yellow crystals of [Pt(S$_2$CNBn$_2$)].py (2). The CHNS data, and % yield of the synthesized complexes are presented below.

Analytical and Spectroscopic Data.

[Pt(S$_2$CN$^i$Bu$_2$)$_2$] (1): Yield: 0.49 g, 81%. Elemental analysis: C$_{18}$H$_{36}$N$_2$S$_4$Pt, Calc: C, 35.80%; H, 6.01%; N, 4.64%; S, 21.24%; Found: C, 35.21%; H, 6.05%; N, 4.55%; S, 21.35%. IR (v/cm$^{-1}$): 2954m, 2923s, 2854s, 1.510s, 1459w, 1430s, 1371s, 1300s, 1278w, 1258s, 1234m, 1219w, 1199m, 1151s, 1119w, 1100s, 1054w, 1029m, 972brs, 793w, 724s, 626w, 606m, 575w, 534w, 518w. $^1$H NMR (400 MHz, DMSO), δ (ppm) 3.83-3.57 (8H, m, 4((CH$_2$CH(CH$_3$)$_2$), 1.8 (4H, m, 4(CH$_2$CH(CH$_3$)$_2$); and 0.87 (24H, s, 4(CH$_2$CH (CH$_3$)$_2$).

[Pt(S$_2$CNBn$_2$)$_2$].py (2): Yield: 0.57 g, 70%. Elemental analysis: C$_{35}$H$_{33}$N$_3$S$_4$Pt, Calc: C, 51.33%; H, 4.06%; N 5.13%; S, 15.66%; Found: C, 50.78%; H, 4.04%; N 4.99%; S, 15.77%. IR (v$_{max}$/cm$^{-1}$): 3062w, 3026m, 2922w, 2322w, 2067brw, 1884brw, 1804w, 1604w, 1585w, 1491s, 1452s, 1427m, 1357s, 1312w, 1253s, 1221s, 1145s, 1076s, 1030s, 989s, 929s, 901w, 882s, 822m, 744s, 736s, 691s, 639w, 626m 585s, 557s, 538s, 516s. $^1$H NMR (400 MHz, CDCl$_3$), δ (ppm) 4.81 (8H, s, 4(CH$_2$)) and 7.26-7.42 (20H, m, aromatic 4(C$_6$H$_5$)) ppm and 7.66-8.62 ppm (5H, m, (NC$_5$H$_5$)).

[Pt(S$_2$CN$^i$Pr$_2$)$_2$] (3): Yield: 0.43 g, 78%. Elemental analysis: C$_{14}$H$_{28}$N$_2$S$_4$Pt, Calc: C, 30.70%; H, 5.15%; N, 5.11%; S, 23.42%. Found: C, 30.84%; H, 4.92%; N, 5.01%, S, 23.55%. IR (v/cm$^{-1}$): 2927s, 2854s, 2091brw, 1596w, 1579m, 1475s, 1460w, 1447w, 1435w, 1366s, 1348s, 1302s, 1270s, 1164s, 1152w, 1108s, 1065w, 1028m, 998s, 949m, 924s, 895s, 883w, 844w, 800w, 747s, 708s, 663s, 613s, 596w, 504w, 489m, 470m. $^1$H NMR (400 MHz, DMSO), δ (ppm) 3.45 (2H, s, 2(NCH(CH$_3$)$_2$), 1.00 (12H, s, 2(NCH (CH$_3$)$_2$).

Instrumentation.

Elemental analyses of the complexes were performed on PerkinElmer Series 11 (CHNS/0), Analyzer 2400. Solid state FTIR spectra of free ligands and their corresponding platinum complexes were recorded on a PerkinElmer FTIR 180 spectrophotometer or NICOLET 6700 FTIR over the range 4000-400 cm$^{-1}$. The $^1$H and $^{13}$C NMR spectra in DMSO were carried out on a JEOL JNM-LA 500 NMR spectrometer at 500.00 MHz and 125.65 MHz operating frequency respectively. The $^{13}$C NMR spectra were recorded with $^1$H broadband decoupling at 297 K. The spectral conditions were; 32 K data points, 0.963 s acquisition time, 3.2 s pulse delay and a 5.75 is pulse width for $^1$H NMR, and 32 K data points, 0.963 s acquisition time, 2.5 s pulse delay and a 5.12 µs pulse width for $^{13}$C NMR. The chemical shifts were measured relative to Tetramethylsilane (MS).

X-Ray Diffraction Analysis.

The intensity data for 1 and 2 were collected at 173K (−100° C.) on a Stoe Mark II-Image Plate Diffraction System (see S. Ahmad, Seerat-ur Rehman, T. Rüffer, T. Khalid, A. A. Isab, A. R. Al-Arfaj, M. Saleem, Ejaz, I. U. Khan, M. A. Choudhary, Monatsch. Chem. 148 (2017) 669-674) equipped with a two-circle goniometer and using MoKα graphite monochromated radiation (λ=0.71073 Å). The structures were solved by direct methods with SHELXS-97; Stoe & Cie. X-Area & X-RED32. Stoe & Cie GmbH, Darmstadt, Germany. (2009). The refinement and all further calculations were carried with SHELXL-2014; G. M. Sheldrick. Acta Cryst. A64 (2008) 112-122. The C-bound H-atoms were included in calculated positions and treated as riding atoms: C—H=0.97-0.99 Å with U$_{iso}$(H)=1.5 U$_{eq}$(C) for methyl H atoms and =1.2 U$_{eq}$(C) for other H atoms. The non-H atoms were refined anisotopically, using weighted full-matrix least-squares on F$^2$. A semi-empirical absorption correction was applied using the MULABS routine in PLATON; G. M. Sheldrick. Acta Cryst. C71 (2015) 3-8. A summary of crystal data and refinement details for complexes 1 and 2 is given in Table 1.

TABLE 1

Crystal data and refinement details for complexes 1 and 2.

| Parameter | 1 | 2 |
|---|---|---|
| Formula | C$_{18}$H$_{36}$N$_2$PtS$_4$ | C$_{30}$H$_{28}$N$_2$PtS$_4$·C$_5$H$_5$N |
| Formula weight | 603.82 | 818.97 |
| Crystal system | Monoclinic | Monoclinic |
| Space group | P2$_1$/c | C2/c |
| a, b, c (Å) | 11.8928(5), 13.0577(5), 16.4868(7) | 20.8211(14), 6.4105(2), 25.3665(17) |
| β (°) | 98.84(3) | 98.766(5) |
| V/Å$^3$ | 2529.84(18) | 3346.2(3) |
| Z | 4 | 4 |
| µ (mm$^{-1}$) | 5.88 | 4.47 |
| Crystal size/mm | 0.40 × 0.40 × 0.40 | 0.45 × 0.17 × 0.13 |
| Temperature (K) | 203 | 203 |
| Wavelength (Å) | 0.71073 | 0.71073 |
| θ value (°) | θ$_{max}$ = 25.6, θ$_{min}$ = 1.7 | θ$_{max}$ = 25.7, θ$_{min}$ = 2.2 |
| T$_{min}$, T$_{max}$ | 0.631, 1.000 | 0.722, 1.000 |
| No. measured, independent and observed [I > 2σ(I)] reflections | 36252, 5087, 4352 | 23293, 3367, 2538 |
| R$_{int}$ | 0.059 | 0.050 |
| R[F$^2$ > 2σ(F$^2$)], wR(F$^2$), S | 0.022, 0.046, 0.95 | 0.017, 0.032, 0.87 |
| Largest diff. peak, hole/e Å$^{-3}$ | 0.79, −0.86 | 0.69, −0.59 |

MTT Assay.

The IC$_{50}$ values in 72 hours of the compounds on human ovarian tumor cell lines, A2780 S (cisplatin sensitive) and A2780 CR (cisplatin resistance) were identified by cell viability test. 6000 cells per well in 100 µL cell media were seeded. After 24 h, all supernatant was aspirated out. Then 200 µL of drug solution is added to the first column of each well, and 100 µL of medium were added into the remaining well. The 100 µL of drug solution from first column was taken and mix well with the next column by repeated pipetting using a multichannel pipettor. The last two columns were leaved without drug addition to serve as blank control. After 72 h, supernatants in each well was replaced with 100 of 10% MTT (3-(4,5-dimethylthiazol-2-yl)-2,5-diphenyltetrazolium bromide) tetrazolium reduction assay solution, and incubated for at least 45 minutes at 37° C. After aspirating incubated solution, 100 µL of DMSO was added into each well to dissolve formazan crystals. The plates were then read using plate reader at 570 nm.

Preparation and Characterization of Complexes.

The complexes were prepared by treating platinum(II) chloride with sodium salts of dithiocarbamates in 1:2 stoichiometric ratio in methanol-pyridine solution as shown by the following chemical reaction. The complexes were isolated as dry crystalline solids, which are readily soluble in common organic solvents, DMSO, pyridine etc. The stoichiometry of the complexes 1-3 was formulated on the basis of elemental analysis. For complexes 1 and 2, it was verified by single crystal X-ray analysis as they were suitable for measurement.

(1)

R = $^i$Bu (1); R = Bn (2); R = $^i$Pr (3)

The IR spectra of the complexes (1)-(3) show typical absorptions in the 1550-1420 cm$^{-1}$ region, which is primarily associated with the stretching vibration of the C—N group of the N—CSS$^-$ moiety. The bands in the region of the 1030-960 cm$^{-1}$ region represent ν(CSS)$_{sym}$ and ν(CSS)$_{asym}$ respectively. The ν(N—CSS) band defines a carbon-nitrogen bond order intermediate between a single bond (ν=1350-1250 cm$^{-1}$) and a double bond (ν=1690-1640 cm$^{-1}$); A. L. Spek. Acta Cryst. D65 (2009) 148-155; M. Sarwar, S. Ahmad, S. Ahmed, S. Ali, S. A. Awan, Transition Met. Chem. 32 (2007) 199-203. The ν(N—CSS) mode of dithiocarbamates is shifted to higher frequency upon coordination consistent with an increase in the carbon-nitrogen double bond character and support the bidentate coordination of the S atoms of dithiocarbamate moieties to the metal center. The ν(N—CSS) value of these complexes is comparable to the other complexes of dithiocarbamates; D. Fregona, L. Giovagnini, L. Ronconi, C. Marzano, A. Trevisan, S. Sitran, B. Biondi, F. Bordin, J. Inorg. Biochem. 93

(2003) 181-189; C. Marzano, D. Fregona, F. Baccichetti, A. Trevisan L. Giovagnini, F. Bordin Chem.-Biol. Interact. 140 (2002) 215-229; D. Montagner, P. J. S. Miguel, Dalton Trans. 40 (2011) 10809-10811; A. L. Spek. Acta Cryst. D65 (2009) 148-155; M. Sarwar, S. Ahmad, S. Ahmed, S. Ali, S. A. Awan, Transition Met. Chem. 32 (2007) 199-203.

The $^1$H NMR spectra of complexes (1)-(3) reveal the usual splitting patterns for protons attached to the corresponding R groups. The $^1$H NMR spectrum of complex 2 shows multiple peaks centered between δ 7.31 and 8.70 ppm due to the protons of pyridine ring. However, such peaks were not observed in the spectra of other two complexes, which suggest the absence of pyridine in their molecular structures.

X-Ray Structures Description.

Figure 1:
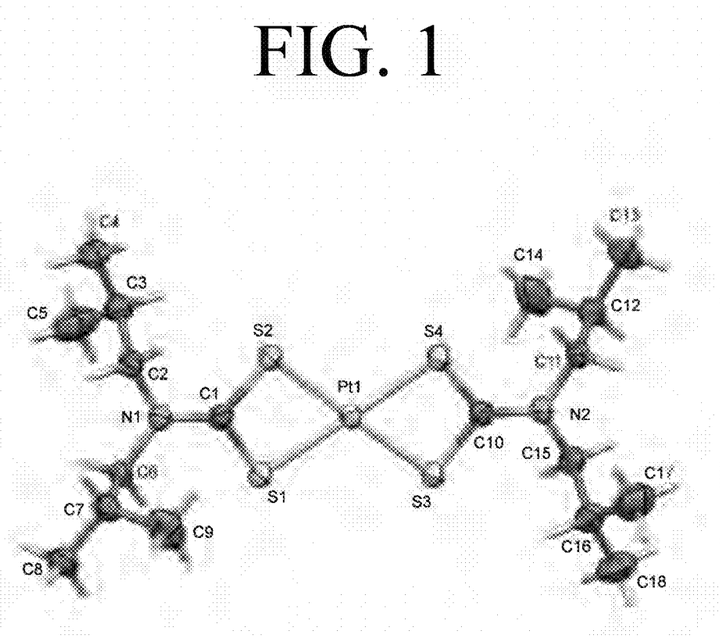
FIG. 1. The molecular structure of complex 1 with atom labeling. The displacement ellipsoids are drawn at the 50% probability level.
Figure 2:
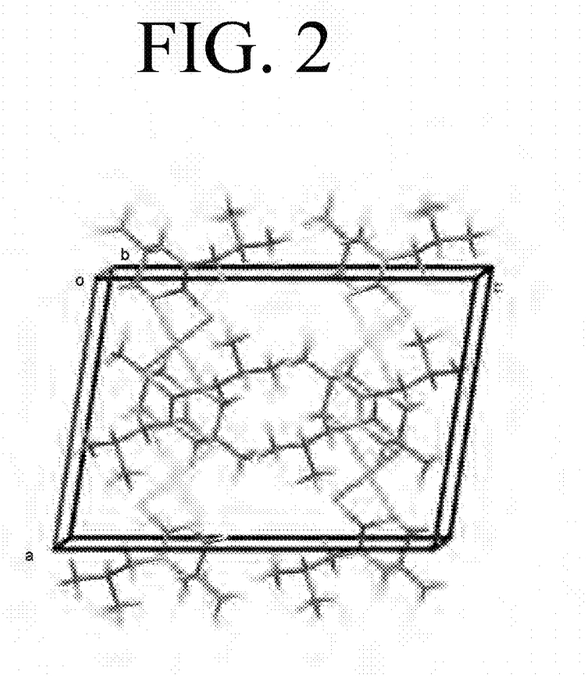
FIG. 2. The crystal packing of complex 1, viewed along the h axis.
Figure 3:
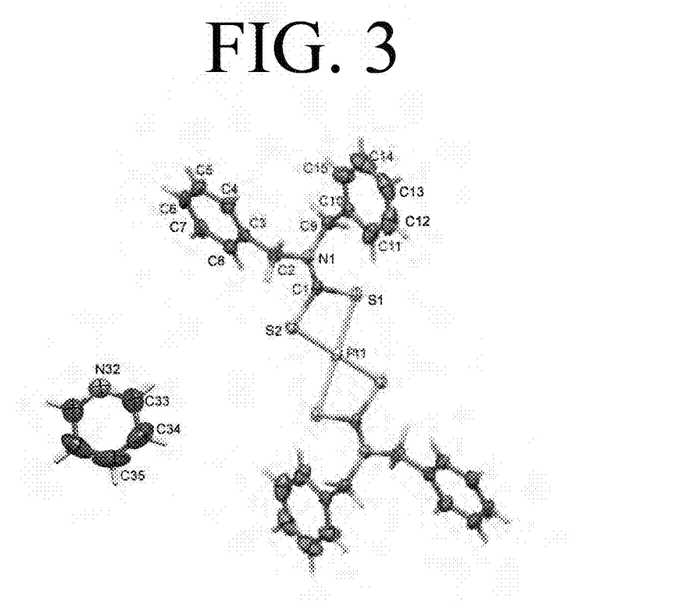
FIG. 3. A view of the molecular structure of complex 2 with atom labeling. The displacement ellipsoids are drawn at the 50% probability level.
Figure 4:
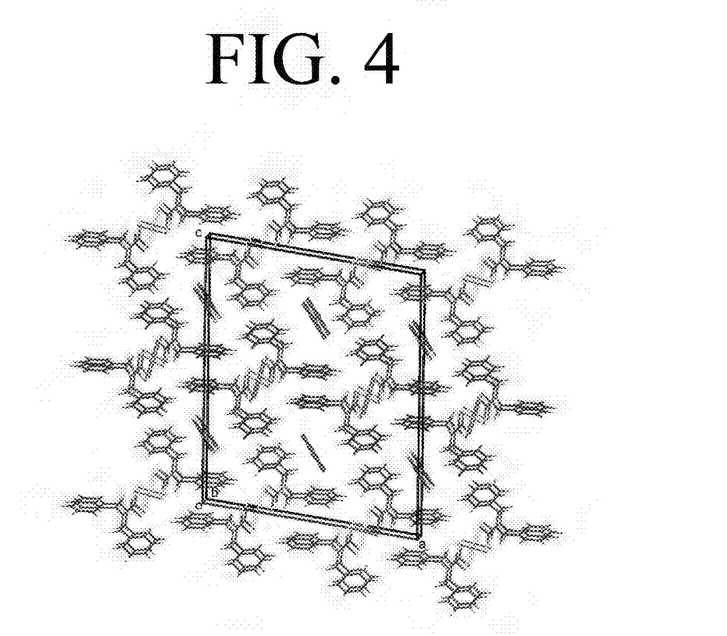
FIG. 4. The crystal packing of complex 2, viewed along the b axis.

The molecular structures of [Pt($S_2$CN$^i$$Bu_2$)$_2$] (1) and [Pt($S_2$CN$Bn_2$)$_2$].py (2) are shown in FIGS. 1 and 3 respectively, while their crystal packing diagrams are shown in FIGS. 2 and 4 respectively. The selected bond distances and bond angles are given in Table 2.

TABLE 2

Particular bond lengths (Å) and bond angles (°) of 1 and 2

| Bond Lengths | | Bond Angles | |
|---|---|---|---|
| (1) | | | |
| Pt1-S1 | 2.3290(8) | S1-Pt1-S2 | 75.06(3) |
| Pt1-S2 | 2.3099(9) | S1-Pt1-S3 | 106.22(3) |
| Pt1-S3 | 2.3255(8) | S1-Pt1-S4 | 178.67(3) |
| Pt1-S4 | 2.3172(8) | S2-Pt1-S3 | 178.72(3) |
| C1-S1 | 1.727(3) | S2-Pt1-S4 | 103.68(3) |
| C1-S2 | 1.729(3) | S3-Pt1-S4 | 75.04(3) |
| N1-C1 | 1.317(4) | N1-C1-S1 | 123.93(12) |
| N1-C2 | 1.481(4) | N1-C1-S2 | 128.61(11) |
| (2) | | | |
| Pt1-S1 | 2.3283(7) | S1-Pt1-S2 | 74.95(2) |
| Pt1-S2 | 2.3159(6) | S1-Pt1-S2$^i$ | 105.05(2) |
| C1-S1 | 1.723(2) | S2-Pt1-S2$^i$ | 180.0 |
| C1-S2 | 1.720(3) | N1-C1-S1 | 123.93(12) |
| N1-C1 | 1319(4) | N1-C1-S2 | 128.61(11) |
| N1-C2 | 1.480(3) | | |

The structure of complex 1 consists of neutral molecules having Pt(II) atom coordinated by two structurally equivalent diisobutyldithiocarbamate ligands. The structure of complex 2 along with neutral complex molecules composed of Pt(II) atom and dibenzyldithiocarbamate, contains a pyridine solvate molecule. In both complexes, the platinum atom lies on a center of inversion and adopts a distorted square planar geometry having the cis bond angles of around 75° and 105°. The trans bond angles in 1 are about 178°, while in 2, they are 180°. The dithiocarbamates bind as symmetrical bidentate ligands. The bidentate binding of two sulfur atoms of the dithiocarbamates to platinum makes the S1-Pt—S2 angle significantly smaller (~75°). The average bond length of ~2.32 Å for the Pt—S bonds is identical with the values found in the analogous Pt-dithiocarbamate complexes; M. K. Amir, Zia-ur-Rehman, F. Hayat, S. Z. Khan, G. Hogarth, T. Kondratyuk, J. M. Pezzutode, M. N. Tahir, RSC Advances, 6 (2016) 110517-110524; G. A. Heath, D. C. R. Hockless, P. D. Prenzler, Acta Cryst. C52 (1996) 537-539.; D. C. Onwudiwe, J. N. Mugo, M. Hrubaru, E. Hosten, J. Sulfur Chem. 36 (2015) 36-47. However, it is somewhat longer than observed in a Pt; metallacycle, [PtCl(pyrrolidinedithiocarbamate)]$_5$; A. T. Baker, M. T. Emett, Aust. J. Chem. 45 (1992) 429-434. The C—S distances in compounds (1) and (2) are almost identical. The shorter N—C ($S_2$) bond lengths in dithiocarbamates compared to N—C(C) distances correspond to a bond order intermediate between single and double bond. In the crystal packing, there are no significant interactions present between the molecules.

Cytotoxic Activity.

Figure 5A:
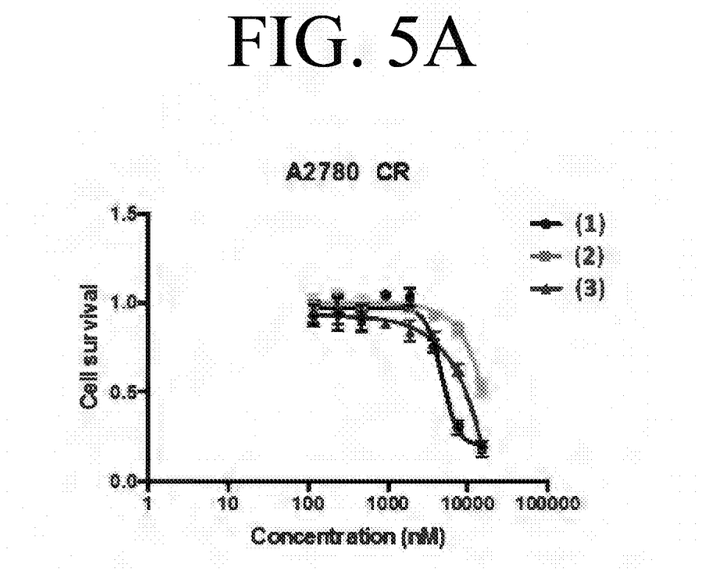
FIGS. 5A and 5B. Cell viability curves of A2780 S/CR cells treated with various concentrations of platinum complexes.
Figure 5B:
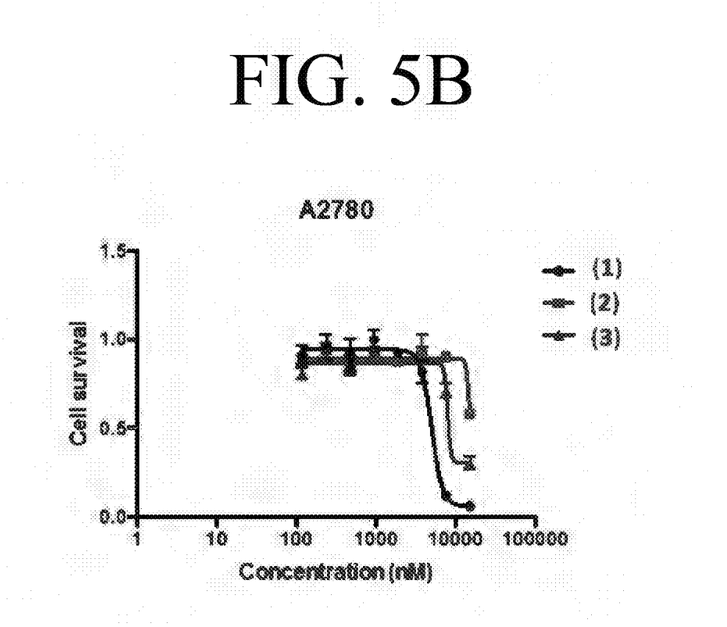

The in vitro cytotoxicity of three platinum complexes (1), (2) and (3) was evaluated against a pair human ovarian tumor cell lines, A2780 S (cisplatin sensitive) and A2780 CR (cisplatin resistant). For comparison, anticancer activity of cisplatin was also evaluated under the same conditions. The $IC_{50}$ values and cell viability curves are shown in Table 3 and FIG. 5 respectively.

TABLE 3

$IC_{50}$ Values (in μM) of Pt(II) compounds against three human tumor cell lines

| Compounds | A2780 S | A2780 CR | Resistance factor |
|---|---|---|---|
| Cisplatin | 0.33 ± 0.011 | 6.37 ± 1 | 19.20 |
| (1) | 5 ± 0.097 | 5.91 ± 0.92 | 1.18 |
| (2) | 16.39 ± 1.35 | 14.99 ± 1.21 | 0.92 |
| (3) | 8.92 ± 0.58 | 8.83 ± 0.83 | 1.00 |

All three platinum complexes showed reasonably good cell killing activity with $IC_{50}$ values in the range of 5±0.097 to 16.39±1.35 and 5.91±0.92 to 14.99±1.21 μM against A2780S and A2780CR cell lines respectively. However, these values are greater than that of cisplatin showing that the complexes exhibit poor cytotoxic effects than cisplatin. The complexes 1 and 3 are found to be more toxic than 2 towards A2780 and A2780 CR cells. Complex 1 was found to be the most effective and also displays better cytotoxicity than cisplatin against A2780 CR cells. The activity is nearly same for both types of cancer cell lines. The lower cytotoxic may be related to the size and strong binding of dithiocarbamate ligands with platinum(II) ion, which would hinder the release of platinum for binding to DNA. On the other hand the platinum complexes containing dithiocarbamate and chloride ligands are labile. Such type of complexes is well known to possess significant antitumor activity; C. Marzano D. Fregona, F. Baccichetti, A. Trevisan, L. Giovagnini, F. Bordin, Chem.-Biol. Interact. 140 (2002) 215-229.

The resistance factors (RF) were also calculated. As can be seen from Table 3, the complexes (1) and (3) showed lower RF number compared to complex (2). This observation provides additional evidence that these complexes can overcome the cisplatin resistance against the cancer cells.

Supplementary Data.

Crystallographic data of compounds 1 and 2 have been deposited with the Cambridge Crystallographic Data Center via the CCDC Numbers 1832275-1832276 and are hereby incorporated by references thereto.

As shown by the Example, three platinum(II) complexes (1)-(3) of the formula, [Pt(dithiocarbamate)$_2$] were synthesized and characterized using various analytical methods. The crystal structures of two complexes (1) and (2) revealed the bidentate binding mode of dithiocarbamates ligands and a distorted square planar geometry around platinum(II). The prepared complexes were tested for in vitro antitumor activity against two human tumor cell lines (A2780 S and A2780 CR), which were found to exhibit reasonably good in vitro cytotoxicity against these cancer cell lines. All the tested complexes showed a lower resistance factor which would help them overcome drug resistance, such as that to cisplatin.

Terminology

Terminology used herein is for the purpose of describing particular embodiments only and is not intended to be limiting of the invention.

The headings (such as "Background" and "Summary") and sub-headings used herein are intended only for general organization of topics within the present invention, and are not intended to limit the disclosure of the present invention or any aspect thereof. In particular, subject matter disclosed in the "Background" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

As used herein, the singular forms "a", "an" and "the" are intended to include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the tell "and/or" includes any and all combinations of one or more of the associated listed items and may be abbreviated as "/".

Links are disabled by deletion of http: or by insertion of a space or underlined space before www. In some instances, the text available via the link on the "last accessed" date may be incorporated by reference.

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values), etc. Any numerical range recited herein is intended to include all sub-ranges subsumed therein.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology. As referred to herein, all compositional percentages are by weight of the total composition, unless otherwise specified. As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present invention that do not contain those elements or features.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page, or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for treating cisplatin-resistant ovarian cancer in a subject in need thereof, the method comprising:
    administering to the subject an amount of at least one complex selected from the group consisting of complex (1): $[Pt(S_2CN^iBu_2)_2]$, complex (2): $[Pt(S_2CNBn_2)_2]\cdot py$, where Bn=benzyl and py=pyridine, and complex (3): $[Pt(S_2CN^iPr_2)_2]$ sufficient to treat cisplatin-resistant ovarian cancer.

2. The method of claim 1, wherein said at least one complex is (1): $[Pt(S_2CN^iBu_2)_2]$.

3. The method of claim 1, wherein said at least one complex is complex (2): $[Pt(S_2CNBn_2)_2]\cdot py$.

4. The method of claim 1, wherein said at least one complex is complex (3): $[Pt(S_2CN^iPr_2)_2]$.

5. The method of claim 1, wherein the complex is administered intravenously.

6. The method of claim 1, wherein the complex is administered intraperitoneally.

7. A complex comprising complex (2): $[Pt(S_2CNBn_2)_2]\cdot py$, where Bn=benzyl and py=pyridine.

8. A pharmaceutical composition comprising the complex (2) of claim 7 and a pharmaceutically acceptable carrier or excipient.

9. The pharmaceutical composition of claim 8 that further comprises an anticancer drug, chemotherapeutic agent, or immunopotentiator.

10. A method for treating cancer comprising administering to a subject in need thereof complex (2): $[Pt(S_2CNBn_2)_2]\cdot py$, where Bn=benzyl and py=pyridine.

11. The method of claim 10, wherein said cancer is ovarian cancer.

\* \* \* \* \*